Figure 1:
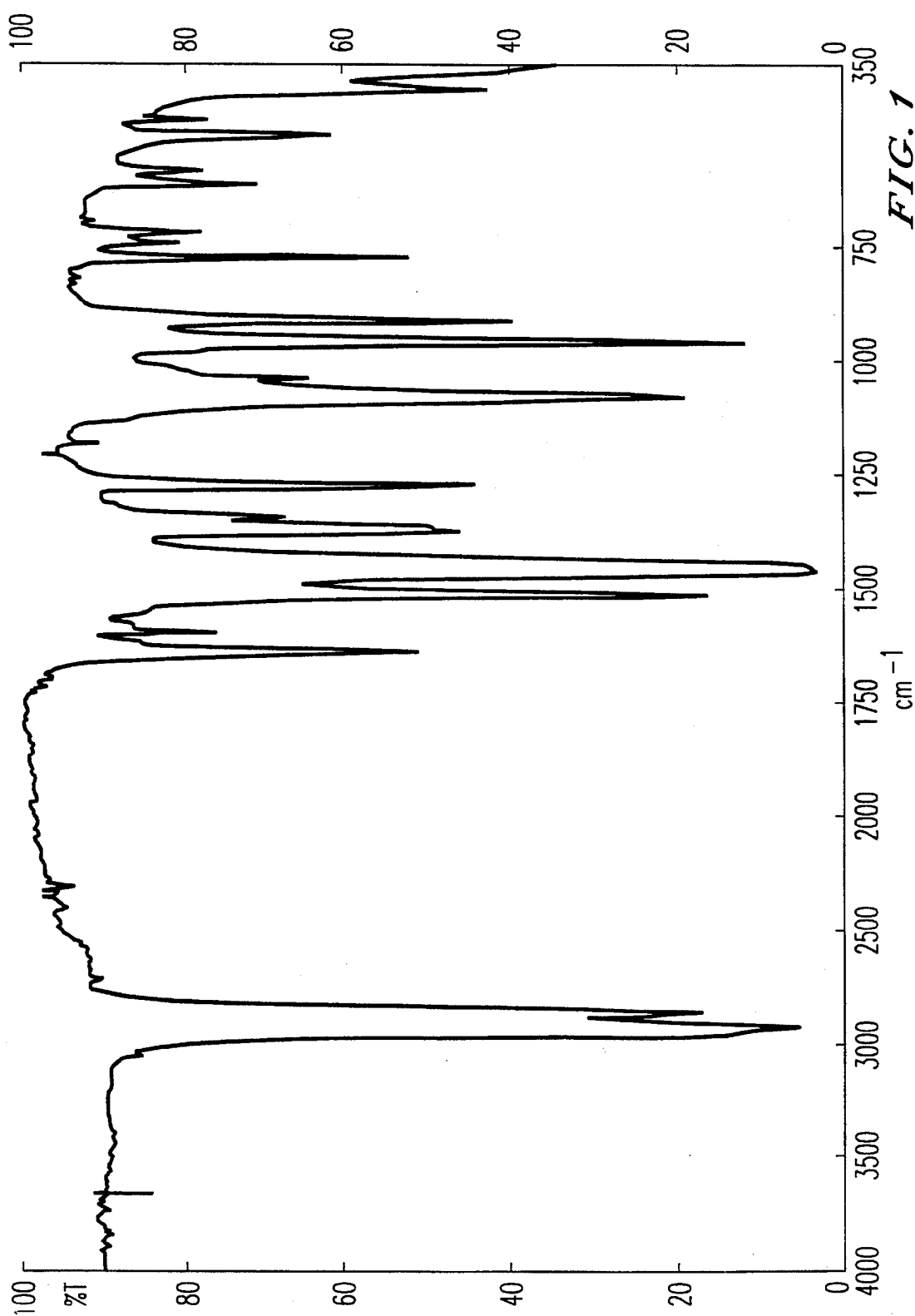

United States Patent [19]

Biagini et al.

[11] Patent Number: 5,602,269

[45] Date of Patent: Feb. 11, 1997

[54] ORGANOMETALLIC DERIVATIVES OF GROUP IIIA AND PROCESS FOR THEIR PREPARATION

[75] Inventors: Paolo Biagini, Trecate; Gabriele Lugli, S. Donato Milanese; Luigi Abis, Cagliari; Piero Andreussi, Milan, all of Italy

[73] Assignee: Enichem Elastomeri S.r.l., Milan, Italy

[21] Appl. No.: 503,618

[22] Filed: Jul. 18, 1995

[30] Foreign Application Priority Data

Jul. 29, 1994 [IT] Italy .................................. MI94A1635

[51] Int. Cl.⁶ ..................................................... C07F 5/06
[52] U.S. Cl. .............................. 556/170; 556/1; 556/187
[58] Field of Search ................................. 556/1, 170, 187

[56] References Cited

PUBLICATIONS

Journal of Organometllic Chemistry, vol. 441, No. 3, pp. 363–371, 1992, K. Ludovici, et al., "Synthesis and Properties of Pentafluorophenylgallium Derivatives. The Preparation of Tris(Pentafluorophenyl)Gallium and Its Adducts, and of Bis(Pentafluorophenyl)Gallium Bromide, Pentafluorophenylgallium Dibromide, and Tetrabutylammonium Tetrakis(Pentafluorophenyl)Gallate".

Chemical Abstracts, vol. 75, No. 19, An 118363X, 1971.

Chemical Abstracts, vol. 74, No. 23, AN 125769S, Jun. 7, 1971.

Primary Examiner—Porfirio Nazario-Gonzalez
Attorney, Agent, or Firm—Oblon, Spivak, McClelland, Maier & Neustadt, P.C.

[57] ABSTRACT

New organometallic derivatives of group IIIA are described having general formula $M(C_6F_5)_3$ wherein M is a metal of group IIIA selected from aluminium, gallium and indium.

The above derivatives are prepared by exchange reaction between a metal alkyl $MR_3$ with an organometallic derivative of boron having the formula $B(C_6F_5)_3$.

8 Claims, 3 Drawing Sheets

ORGANOMETALLIC DERIVATIVES OF GROUP IIIA AND PROCESS FOR THEIR PREPARATION

The present invention relates to new organometallic compounds of aluminium, gallium and indium and the process for their preparation.

More specifically the present invention relates to new compounds having the general formula $M(C_6F_5)_3$, wherein M is a metal of the group IIIA of the periodic table of elements selected from Al, Ga, In, and the group $C_6F_5$— represents an aromatic ring of the benzenic type wherein all the hydrogen atoms have been substituted with fluorine atoms.

Patent and scientific literature amply describe the preparation of catalytic systems of the Ziegler-Natta type for the stereospecific polymerization of olefinic or diolefinic unsaturated monomers.

These catalytic systems generally consist of the salts of transition metals combined with organometallic compounds of metals belonging to groups IA, IIA and IIIA of the periodic table of elements, used as reducing or alkylating agents of the transition metal. Among these reducing or alkylating compounds, the derivatives of Aluminium with the general formula $AlR_3$, wherein R represents an aliphatic, cycloaliphatic or aromatic alkyl radical, are the most important.

Numerous references are also made on how the nature of the Aluminium alkyl influences the activity and stereospecificity of the catalytic systems.

Detailed information on the use of these derivatives of Aluminium in Ziegler-Natta catalysis can be found in the book of G. Allen and J. Bevington "Comprehensive Polymer Science", Pergamon Press, 1989, pages 1–108 and in the vast literature quoted therein.

The known art describes different methods for the synthesis of phenyl derivatives of metals of group IIIA, such as $Al(C_6H_5)_3$, wherein the phenyl radical does not contain fluorine atoms.

G. Wittig and D. Wittenberg (Annalen der Chemie, vol. 606, pages 1–23 of 1957) describe the preparation of $Al(C_6H_5)_3$ by the reaction of lithium-phenyl or a Grignard compound having the formula $C_6H_5$—Mg—Cl with aluminium trichloride in an ether solvent. $Al(C_6H_5)_3Et_2O$ is obtained from which, by heating to 160° C. and $10^{-6}$ Pa ($10^{-3}$ mm Hg), the derivative $Al(C_6H_5)_3$ can be obtained without ether.

Similarly, U.S. Pat. No. 2,960,516 describes the preparation of $Al(C_6H_5)_3$ starting from an iso-octanic solution of sodium phenyl and reacting it with a solution of $AlCl_3$ in ethyl ether. Also in this case, as in the previous one, pure $Al(C_6H_5)_3$ is obtained by decomposition of the complex with ether at 140° C.

T. Mole in Australian Journal of Chemistry, vol. 16, pages 794–800 of 1963, discloses the preparation of $Al(C_6H_5)_3$ starting from the Grignard compound $C_6H_5$—Mg—Br through the formation of the intermediate derivative of mercury $Hg(C_6H_5)_2$, from which $Al(C_6H_5)_3$ is obtained by reaction with metallic aluminium in toluene at boiling point.

Finally, DE-A 1,057,600 describes the preparation of $Al(C_6H_5)_3$ by exchange reaction between $B(C_6H_5)_3$ and $Al(C_2H_5)_3$. In this case it is compulsory to heat the reaction mixture to 140° C. and distill the reaction product $B(C_2H_5)_3$ be able to obtain the desired compound in its pure state.

With respect to the preparation of the organometallic compounds claimed in the present invention, scientific literature describes two attempts at the synthesis, both unsuccessful, of the derivative $Al(C_6F_5)_3$.

For example, J. L. Pohlmann (Zeitschrift fur Naturforschung, vol. 20b, page 5 of 1965) describes the synthesis of the etherate complex $Al(C_6F_5)_3Et_2O$ through the reaction of $AlCl_3$ and $C_6F_5$—Mg—Br in ether. The attempt to remove the ether molecule from the complex by heating to over 100° C., caused a violent explosion of the reation mixture. Similarly, the attempt at synthesis by exchange reaction starting from $B(C_6F_5)_3$ and $Al(C_2H_5)_3$ and the subsequent heating of the reaction mass to distill the volatile $B(C_2H_5)_3$ derivative also failed. R. D. Chambers (Journal of the Chemical Society, 1967, page 2185) subsequently confirmed these negative results.

A new process has now been found which leads to the formation of new derivatives with the general formula $M(C_6F_5)_3$. It has been found in fact that compounds with the general formula $M(C_6F_5)_3$, wherein M is Aluminium, Gallium or Indium, can be easily prepared by exchange reaction between a derivative of boron having the formula $B(C_6F_5)_3$ and trialkyls of the metal of interest having the general formula $MR_3$. With the above process the precipitation of the derivative $M(C_6F_5)_3$ takes place. As the reaction is carried out in a hydrocarbon solvent, the desired compound precipitates without co-ordinated ether molecules, which would prevent its being obtained in its pure state, as already specified in literature.

In accordance with this, the present invention relates to compounds having general formula (I) $M(C_6F_5)_3$, wherein M is a metal of the group IIIA selected from Aluminium, Gallium and Indium, preferably Aluminium.

The present invention also relates to a process for the preparation of $M(C_6F_5)_3$ wherein M has the above meaning, characterized in that $B(C_6F_5)_3$ and $M(H)_nR_m$ are reacted in a basically hydrocarbon solvent according to the following scheme (A):

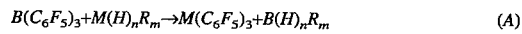

$$B(C_6F_5)_3 + M(H)_nR_m \rightarrow M(C_6F_5)_3 + B(H)_nR_m \qquad (A)$$

M is a metal of the group IIIA selected from Aluminium, Gallium and Indium, preferably Aluminium;

R is selected from aliphatic, cycloaliphatic, benzylic, linear or branched, monofunctional radicals, containing from 1 to 20 carbon atoms, and is preferably selected from methyl, ethyl and isobutyl;

n+m=3; n is 0 or 1.

In the preferred embodiment, m=3.

The organometallic compound of boron, $(B(C_6F_5)_3$, used as reagent in scheme (A), was prepared as already described in scientific literature, by reacting a derivative of magnesium having the formula $(C_6F_5)$—Mg—Br, obtained from $C_6F_5$—Br and Mg in flakes, with $BF_3.Et_2O$ in ethyl ether.

The compound $M(H)_nR_m$ is a derivative of di- or trialkyls of Aluminium, Gallium or Indium.

This can also be obtained with the methods already described in scientific literature, but in the case of aluminium, valid derivatives which can be used for the purposes of the present invention, such as for example:

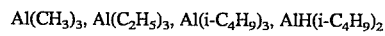

$Al(CH_3)_3$, $Al(C_2H_5)_3$, $Al(i-C_4H_9)_3$, $AlH(i-C_4H_9)_2$ are already available on the market.

The reaction according to scheme (A) is carried out in a basically aliphatic, cycloaliphatic or aromatic, hydrocarbon solvent, by mixing solutions of the reagents $B(C_6F_5)_3$ and $M(H)_nR_m$ in the above solvents.

The molar ratios of the reagents indicated in scheme (A) are maintained, for reasons of convenience, simplicity of the reaction and purity of the final product $M(C_6F_5)_3$, at basically 1:1.

In fact, if an excess of the reagent $B(C_6F_5)_3$ is used, part of this must be recovered at the end of the reaction as it is the most expensive component; in addition the isolation of the desired product in its pure state is more difficult.

If, on the contrary, an excess of the component $M(H)_nR_m$ is used, the purity of the final product is jeopardized as, at the end of the reaction, besides the expected products $B(H)_nR_m$ and $M(C_6F_5)_3$, there will also be consistent quantities of mixed products of the type $M(C_6F_5)_nR_{3-n}$ with n=1 and 2.

The reaction temperature is not determinant for obtaining the final product if the reaction is carried out within the range $-20°\pm100°$ C. It is preferable however to operate at a temperature of between 0° and 30° C.

In general, the reaction is carried out by dissolving the derivative $B(C_6F_5)_3$ in toluene or hexane and adding, under stirring, to the solution thus obtained, a solution of $M(H)_nR_m$ in the same solvent. Basic solvents must be avoided or those which would sensitively interact with the derivatives of Boron or the metal of group IIIA (for example amines, water, alcohols, ethers).

As all the compounds involved, reagents and products, are highly sensitive to oxygen or humidity, or both, all the reaction phases and subsequent isolation of the desired product, must be strictly carried out under an inert gas using the well-known nitrogen-vacuum technique.

After a time ranging from a few seconds to several hours, depending on the type of R and M and solvents used, the solution becomes torbid because of the formation of an abundant white precipitate consisting of the desired product $M(C_6F_5)_3$ in its pure state. The quantity of the product $M(C_6F_5)_3$ which precipitates depends on the operating conditions used and varies from 40% to 70% of the equivalents of the metal used in the reaction. After this first precipitation the mother liquor of the reaction can be concentrated at room temperature or cooled to a low temperature obtaining further quantities of microcrystalline product. The final yield of dried crystallized product varies from 70% to 90%, calculated on $M(H)_nR_m$ used as reagent.

As already specified above, the reaction solvent basically consists of an aliphatic, cycloaliphatic or aromatic hydrocarbon from which the product precipitates and can be recovered by filtration and subsequent drying under vacuums for several hours.

When an aromatic solvent is used, for example toluene or benzene, the final product, recovered as a crystalline solid after drying at room temperature, contains a mole of solvent per mole of derivative and the final product is therefore better represented by the general formula $M(C_6F_5)_3$ (solvent). The molecule of solvent can be easily removed if the drying step is carried out under vacuum at 80° C., without the desired final product, $M(C_6F_5)_3$, undergoing any decomposition, as shown from chemical analyses and NMR and infrared spectra.

When, on the other hand, an aliphatic solvent is used, the drying of the recovered solid can be carried out directly at room temperature under the vacuum of a mechanical pump, to obtain the desired product without the solvent.

Figure 2:
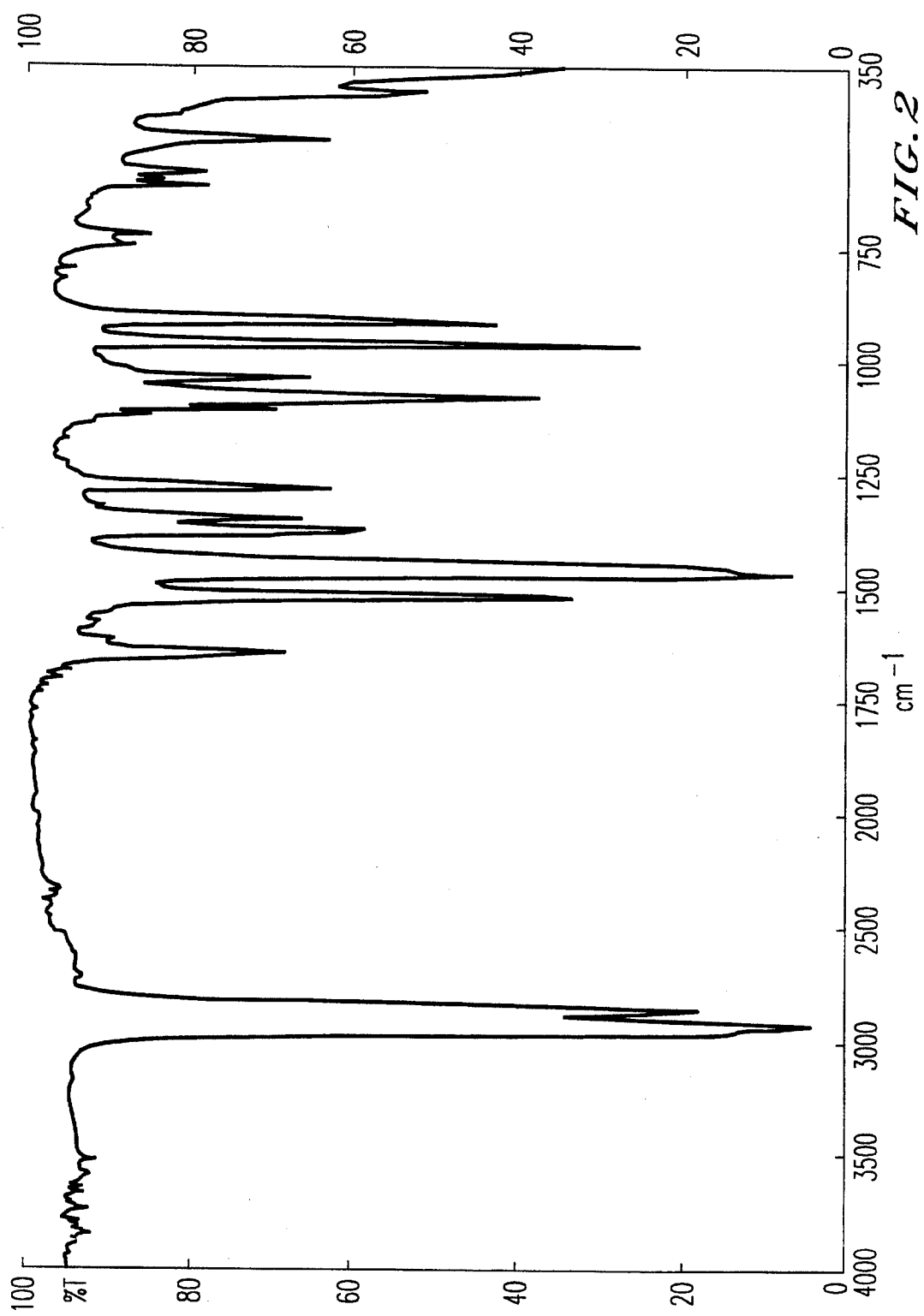
Figure 3:
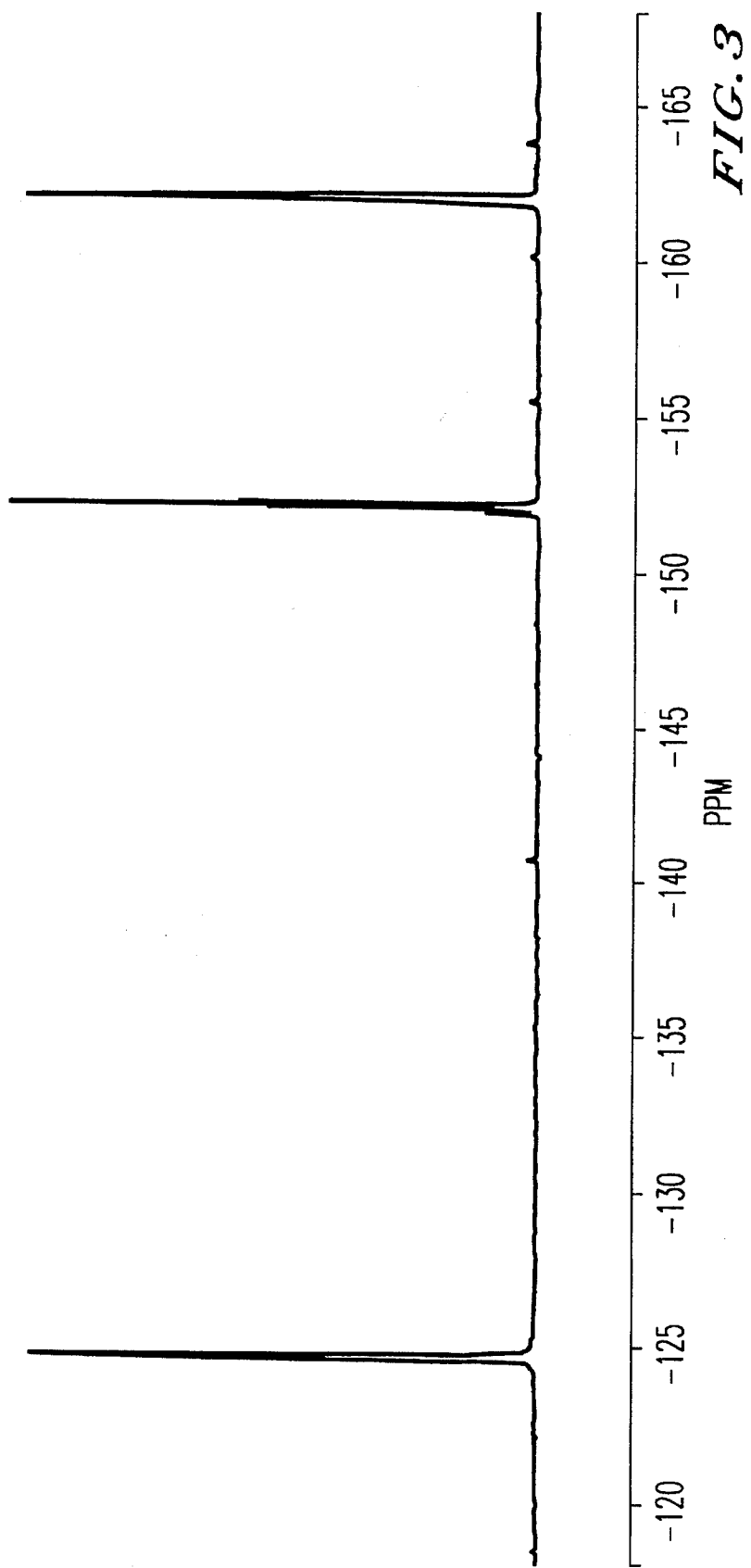

In the case of $Al(C_6F_5)_3$, the chemical nature of the product, was identified not only by chemical analyses of the solid, but also by means of its infrared spectrum (FIGS. 1 and 2) and NMR spectrum of the $^{19}F$ (FIG. 3). The infrared spectrum also permitted the presence of the toluene molecule to be revealed in the crystal obtained by drying at room temperature and its disappearance after heating the crystalline solid to 80° C.

The NMR spectrum of the $^{19}F$ (in toluene-$d_8$ at 243 K.), shown in FIG. 3, showed that only three signals of fluorine exist in the molecule at $\delta=-124.6, -152.1, -162.0$ ppm (taking the signal at $\delta=-78.5$ ppm of the $CF_3COOD$ in toluene-$d_8$ as external reference), with a relative intensity of 2:1:2. This trend of the spectrum can be explained by attributing the three signals, in order, to the fluorine atoms in ortho, para and meta position with respect to the carbon bound to the aluminium atom in the —$C_6F_5$ rings. The presence of only three types of resonances for the fluorine atom shows that the three $C_6F_5$ rings are equivalents and therefore the $Al(C_6F_5)_3$ compound is monomeric. In fact, the formation of a dimer would cause a differentiation of the —$C_6F_5$ rings with an increase of the number of signals relating to fluorine.

The products having general formula (I), particularly those wherein M is Al, can be advantageously used as cocatalysts in the Ziegler-Natta polymerization of olefins and diolefins.

With respect to the enclosed figures, number 1 is the IR spectrum in nujol of $Al(C_6F_5)_3$ (toluene), FIG. 2 is the IR spectrum in nujol of $Al(C_6F_5)_3$ after drying at 80° C. for 8 hrs under vacuum ($10^{-5}$ Pa), FIG. 3 is the NMR spectrum of $^{19}F$ of $Al(C_6F_5)_3$ in toluene-$d_8$ at 243 K. (the chemical shifts refer to $CF_3COOD$ in toluene-$d_8$ taken as external standard at $\delta=-78.5$ pm).

The following examples provide a better understanding of the present invention.

EXAMPLE 1

An illustration is given of the preparation of the reagent $B(C_6F_5)_3$ all the operations being strictly carried out without air and humidity. A 1 liter three-necked flask equipped with reflux cooler, mechanical stirrer and drip funnel is accurately subjected to a dry nitrogen flow to remove all traces of oxygen and humidity. The flask is then charged with 350 cm$^3$ of ether, anhydrified by boiling with sodium hydride, and 20 g of magnesium chips. Maintaining the flask at room temperature, 22 cm$^3$ (0.176 moles) of bromine-pentafluorobenzene are slowly added dropwise from the drip funnel in a time of 2 h. At the end of the addition the reaction mixture is stirred for a further 3 hrs at room temperature, filtered and on the filtrate the so formed Grignard compound is determined by the acidimetric titration of an aliquot of the solution, which proves to contain 0.15 total moles of the Grignard reagent. The solution is dripped, in a time of 2 hrs, into a solution of 7.1 grams of boron-trifluoride etherate in 40 cm$^3$ of ethyl ether maintained under stirring at 0° C. The final reaction mixture is maintained under stirring for a further two hours at room temperature, the solvent is then removed under vacuum and the residue is dried at 50° C. for 4 hrs at $10^{-5}$ Pa.

The solid obtained is subjected to sublimation at $10^{-6}$ Pa obtaining 21 g of $B(C_6F_5)_3$ with a calculated yield of 82% of boron trifluoride etherate.

EXAMPLE 2

An illustration is given of the preparation of $Al(C_6F_5)_3$ starting from $B(C_6F_5)_3$ and $Al(CH_3)_3$. All the operations are carried out under inert gas using the well-known nitrogen-vacuum technique; the solvents were anhydrified by distillation on sodium hydride.

75 cm$^3$ ($13.5\times10^{-3}$ moles) of an 0.18 molar solution of $B(C_6F_5)_3$ in toluene are charged into a graduated test-tube equipped with a magnetic anchor for the stirring and a lateral tap to keep it under a flow of anhydrous nitrogen. 10.0 cm$^3$ ($13.6\times10^{-3}$ moles) of a 1.36 molar solution of $Al(CH_3)_3$ in toluene are added dropwise under magnetic stirring. The solution remains limpid for about 2 hrs and then becomes progressively turbid and a microcrystalline solid begins to precipitate. The suspension is left to rest for 12 hrs and is then filtered on a septum and the solid, washed twice with a total of 39 cm$^3$ of hexane, is dried at room temperature under a vacuum of 10$^{-5}$ Pa for 4 hrs, collected and weighed (5.5 g). The mother liquor also containing the washing hexane, is concentrated at 40 cm$^3$ and thermostated at $-24°$ C. for a night. A second portion of crystalline material precipitates which, after drying, is collected and weighed (1.7 g). Both of the solids have an Al Value of 4.18% against a calculated value of 4.35% for Al(C$_6$F$_5$)$_3$ (toluene) and have the same infrared spectrum which is shown in FIG. 1. The total yield of the reaction is 85%, calculated in the Al(C$_6$F$_5$)$_3$ derivative (toluene) on the basis of the starting aluminium trimethyl.

3.5 grams of the product are heated to 80° C. under a dynamic vacuum of 10$^{-5}$ Pa for 12 hrs. At the end the chemical analysis of the aluminium is repeated on the residual solid and proves to be 5.0% against a calculated value of 5.11% for Al(C$_6$F$_5$)$_3$. The corresponding infrared spectrum of the product after drying is shown in FIG. 2.

EXAMPLES 3–5

Operating as described in example 2, the reaction is carried out between B(C$_6$F$_5$)$_3$ and Al(C$_2$H$_5$)$_3$ (example 3), Al(i-C$_4$H$_9$)$_3$ (example 4) and AlH(i-C$_4$H$_9$)$_2$ (example 5), in toluene at room temperature and using an equimolar ratio between the boron derivative and the aluminium alkyl.

In example 3, 0.125 moles of B(C$_6$F$_5$)$_3$ and 0.125 moles of Al(C$_2$H$_5$)$_3$ in 400 cm$^3$ of toluene are used. 0.109 moles are obtained (yield=88%) of Al(C$_6$F$_5$)$_3$ (toluene). The content of aluminium is 4.20% (theoretical value, referring to Al(C$_6$F$_5$)$_3$ (toluene), 4.35%).

In example 4, 0.055 moles of Al(i-C$_4$H$_9$)$_3$ and 0.055 moles of B(C$_6$F$_5$)$_3$ in 200 cm$^3$ of toluene are used. 0.043 moles are obtained (yield=79%) of Al(C$_6$F$_5$)$_3$(toluene). The content of aluminium is 4.11% (theoretical value, again referring to the complex with toluene, 4.35%).

In example 5, 0.059 moles of AlH(i-C$_4$H$_9$)$_2$ and 0.059 moles of B(C$_6$F$_5$)$_3$ in 250 cm$^3$ of toluene are used. 0.038 moles of Al(C$_6$F$_5$)$_3$(toluene) are obtained. The content of aluminium is 4.27% against the theoretical value of 4.35%.

EXAMPLE 6

Operating as described in example 2, the reaction is carried out between B(C$_6$F$_5$)$_3$ and Al(C$_2$H$_5$)$_3$ at room temperature in an aliphatic solvent. In this way, 5.63 g (0.011 moles) of B(C$_6$F$_5$)$_3$ in 240 cm$^3$ of hexane are reacted with 1.25 g (0.11 moles) of Al(C$_2$H$_5$)$_3$. Within an hour an abundant precipitate is formed which is filtered, washed twice with hexane, and dried with the mechanical pump at room temperature.

4.0 grams of Al(C$_6$F$_5$)$_3$ are recovered with a calculated yield of 69% of Al(C$_2$H$_5$)$_3$.

We claim:

1. A compound of the formula (I): M(C$_6$F$_5$)$_3$, wherein M is aluminum.

2. A process for the preparation of a compound having formula (I): M(C$_6$F$_5$)$_3$, which comprises:

reacting B(C$_6$F$_5$)$_3$ with a compound having the formula: M(H)$_n$R$_m$, wherein M is aluminum and R is a member selected from the group consisting of aliphatic, cycloaliphatic, benzylic, linear or branched, monofunctional radicals containing from 1 to 20 carbon atoms; n+m=3 and n is 0 or 1.

3. The process of claim 2, wherein R is methyl, ethyl or isobutyl.

4. The process of claim 3, wherein the molar ratio of B(C$_6$F$_5$)$_3$ to M(H)$_n$R$_m$ is about 1:1.

5. The process of claim 2, wherein the reaction occurs in a hydrocarbon solvent.

6. The process of claim 2, wherein the reaction is conducted at a temperature ranging from $-20°$ C. to 100° C.

7. The process of claim 6, wherein the reaction temperature ranges from 0° C. to 30° C.

8. The process of claim 2, wherein M is aluminum, m=3 and R is methyl, ethyl or isobutyl.

* * * * *